United States Patent [19]

Moriuchi

[11] Patent Number: 5,084,015

[45] Date of Patent: Jan. 28, 1992

[54] CATHETER ASSEMBLY OF THE HYPODERMIC EMBEDMENT TYPE

[75] Inventor: Yousuke Moriuchi, Fuji, Japan

[73] Assignee: Terumo Kabushiki Kaisha, Tokyo, Japan

[21] Appl. No.: 459,821

[22] PCT Filed: May 15, 1989

[86] PCT No.: PCT/JP89/00490

§ 371 Date: Jan. 11, 1990

§ 102(e) Date: Jan. 11, 1990

[87] PCT Pub. No.: WO89/11309

PCT Pub. Date: Nov. 30, 1989

[30] Foreign Application Priority Data

May 16, 1988 [JP] Japan .................. 63-118839

[51] Int. Cl.$^5$ .................................. A61M 31/00
[52] U.S. Cl. .................................. 604/96; 604/9; 604/93; 604/185; 606/191
[58] Field of Search ............ 604/93, 96, 101, 102, 604/185, 173, 175, 183, 186, 8-10; 606/191, 194

[56] References Cited

U.S. PATENT DOCUMENTS

| 4,588,394 | 5/1986 | Schulte et al. ............. | 604/185 |
| 4,673,394 | 6/1987 | Fenton, Jr. et al. . | |
| 4,685,447 | 8/1987 | Iversen et al. ............. | 604/103 |
| 4,692,146 | 9/1987 | Hilger .......................... | 604/93 |
| 4,710,174 | 12/1987 | Moden et al. . | |
| 4,782,834 | 11/1988 | Maguire et al. ............. | 604/96 |
| 4,798,584 | 1/1989 | Hancock et al. ............ | 604/93 |
| 4,850,969 | 7/1989 | Jackson ....................... | 604/102 |

FOREIGN PATENT DOCUMENTS

| 0260081 | 9/1987 | European Pat. Off. . |
| 59-177064 | 10/1984 | Japan . |
| 62-155857 | 7/1987 | Japan . |
| 62-281966 | 12/1987 | Japan . |
| 63-38535 | 3/1988 | Japan . |
| 64-11562 | 1/1989 | Japan . |
| WO87/06473 | 4/1987 | World Int. Prop. O. . |

OTHER PUBLICATIONS

Japanese Journal of Cancer and Chemotherapy, 1984, vol. 11, No. 4.

Primary Examiner—Richard J. Apley
Assistant Examiner—Rachel M. Healey
Attorney, Agent, or Firm—Frishauf, Holtz, Goodman & Woodward

[57] ABSTRACT

A catheter assembly of the hypodermic embedment type for infusing a fluid medicament such as a carcinostatic agent into a body cavity such as a blood vessel for therapeutic purposes, includes a medicament infusion implement having an inlet port and an outlet port and a catheter connected to the implement outlet port. The device is used by inserting and indwelling the catheter in a body cavity and embedding the implement beneath the skin. Treatment can be repeated any number of desired times with the catheter assembly kept indwelled in the body, resulting in a significant reduction of the burden to the patient as compared with the prior art technique requiring insertion and withdrawal of a catheter every time when treatment is made. Also, the danger of infection during the treatment is eliminated, as compared to the prior art technique where the catheter is percutaneously inserted.

18 Claims, 5 Drawing Sheets

CATHETER ASSEMBLY OF THE HYPODERMIC EMBEDMENT TYPE

FIELD OF THE INVENTION

This invention relates to a catheter assembly of the hypodermic embedment type which is used by embedding beneath the skin and indwelling in a body cavity such as a blood vessel, and more particularly, to a catheter assembly of the hypodermic embedment type useful in therapeutic intraarterial transfusion of fluid medicaments such as carcinostatic agents.

BACKGROUND OF THE INVENTION

Chemotherapy based on administration of carcinostatic agents is usually taken against malignant tumors which cannot be removed by ablation. Since general administration gives significant side-effects, strict limits must be imposed to the amount of medicament administered and the administration period, making it difficult to establish an effective concentration of the medicament in the tumor tissue.

To compensate for such a drawback of the chemotherapy using carcinostatic agents, intraarterial transfusion of carcinostatic agents is often employed as a therapy for allowing the medicaments to act on tumor sites at as high concentrations as possible.

One of the intraarterial transfusion therapies is an embolic chemotherapy using a balloon catheter (Cancer and Chemotherapy, Vol. 11, No. 4, pages 806-813, 1984).

This therapy involves inserting a balloon catheter through the femoral artery with the aid of an introducer, adjusting the expansion and contraction of the balloon under X-ray fluoroscopic observation, allowing the distal end of the balloon catheter to be carried by the blood flow to a destined site (an upstream position in the artery leading to the tumor site), then causing the balloon to expand to shut off the blood flow, and thereafter admitting a carcinostatic agent to the destined site through a lumen in the balloon catheter.

According to this technique, once the blood flow in the artery associated with a cancer carrying organ is temporarily shut off, the medicament is admitted to the distal side. Thus the medicament advantageously reaches the tumor at a high concentration without being diluted with blood and stays thereat for an extended period, achieving an enhanced curing effect.

However, this technique has the following drawbacks.

(1) It requires a skill to insert the balloon catheter to the destined site.

(2) Since the balloon catheter is percutaneously inserted, prolonged indwelling would increase the risk of infection.

(3) Although administration of medicament to the tumor is repeatedly carried out over a long period of time, the balloon catheter should be inserted and withdrawn every time when treatment is done in order to avoid potential infection, imposing an increased burden to the patient.

(4) Since angiography is sometimes required to evaluate the curing effect, a catheter must be additionally inserted for admitting a radiopaque agent.

SUMMARY OF THE INVENTION

An object of the present invention is to eliminate the above-mentioned drawbacks of the prior art techniques and to provide a catheter assembly of the hypodermic embedment type which allows for indwelling for an extended period of time and repetitive treatments with ease, but without potential infection.

This and other objects can be attained by the present invention as defined below.

According to a first aspect of the present invention, there is provided a catheter assembly of the hypodermic embedment type comprising a hypodermically embedable medicament infusion implement including a housing and at least one inlet port and at least one outlet port both in communication with said housing, and a catheter, said assembly being used by embedding its entirety under the skin, characterized in that the outlet port of said medicament infusion implement is connected to a proximal end of said catheter, and said inlet port has mounted therein a resilient member which can allow insertion of a needle and self close off after withdrawal of the needle.

According to a second aspect of the invention, three is provided a catheter assembly of the hypodermic embedment type as defined above wherein said medicament infusion implement includes at least two inlet ports and at least two outlet ports for fluid medicament infusion.

According to the present invention, a catheter assembly of the hypodermic embedment type, which is used by being embedded in its entirety under the skin, comprises a hypodermically embedable medicament infusion implement including a housing and at least one inlet port at least one outlet port, said at least one inlet port and at least one outlet port being in communication with said housing; and a balloon catheter having distal and proximal ends, and having a balloon at said distal end thereof. The at least one outlet port of said medicament infusion implement is connected to said proximal end of said catheter; and the at least one inlet port has mounted therein a resilient member which allows insertion of a needle and which self closes off after withdrawal of the needle. The medicament infusion implement further includes a first chamber for balloon inflation and a second chamber for medicament infusion defined in said housing, a first inlet port and a first outlet port in communication with said first chamber, and a second inlet port and a second outlet port in communication with said second chamber. The first and second inlet ports having at least one dimension which is different from each other. The balloon catheter includes a tube body having a distal end, at least one expandable and contractible balloon disposed around the periphery of said tube body near said distal end of said tube body, a first lumen formed in said tube body in communication with said balloon, and a second lumen formed in said tube body and opening at a further distal end portion of said tube body beyond said balloon. The first lumen has a proximal end connected to said first outlet port and the second lumen has a proximal end connected to said second outlet port.

According to a further feature of the invention, the medicament infusion implement further includes a third chamber for medicament infusion defined in said housing; and a third inlet prot and a third outlet port in communication with said third chamber. The balloon catheter further includes a third lumen formed in said tube body and opening at said further distal end portion of said tube body beyond said balloon; and said third lumen has a proximal end connected to said third outlet port.

THE BEST MODE FOR CARRYING OUT THE INVENTION

The catheter assembly of the hypodermic embedment type according to the present invention will be described in detail in conjunction with its preferred embodiments shown in the accompanying drawings.

Figure 1:
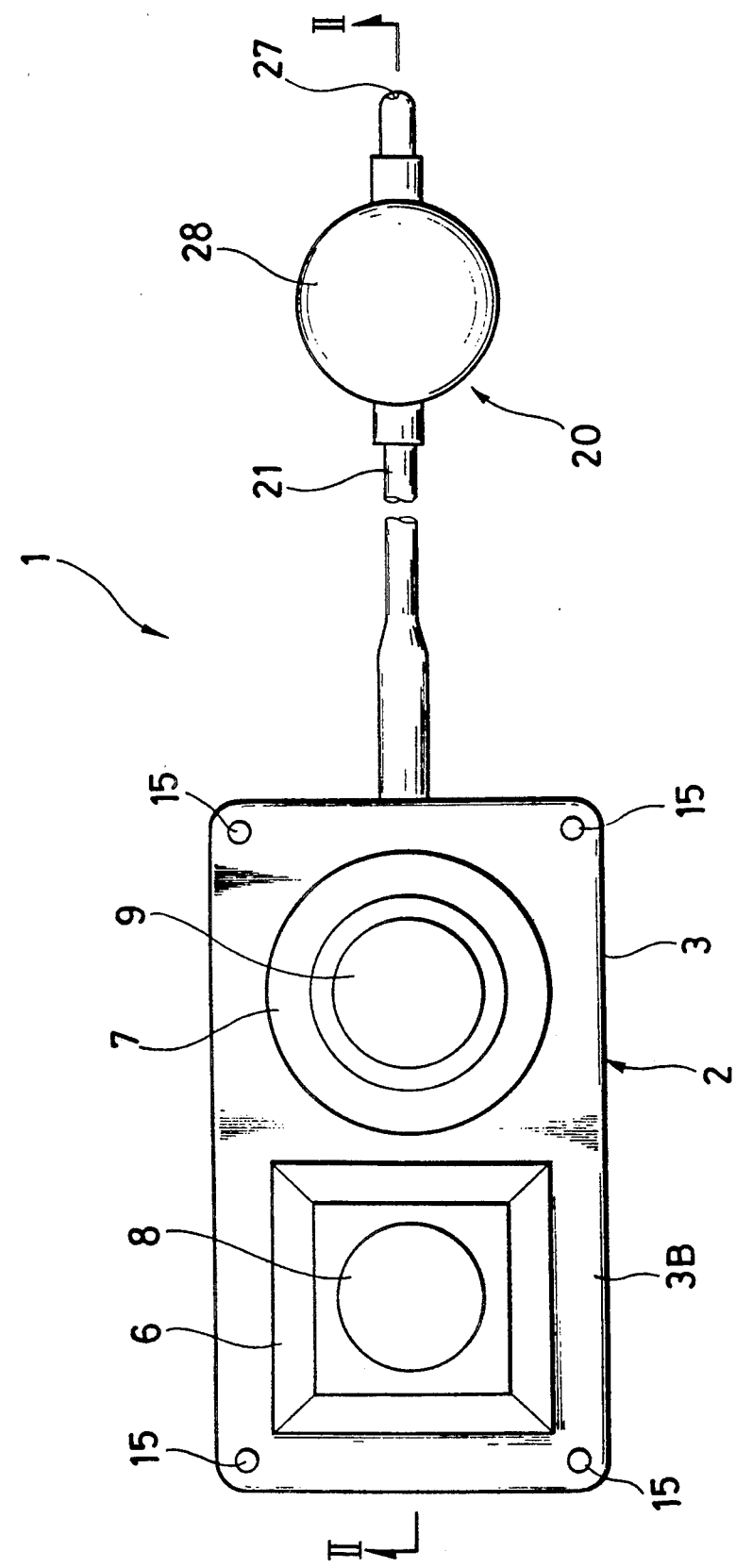
FIG. 1 is a plan view of a catheter assembly of the hypodermic embedment type according to one embodiment of the present invention.
Figure 2:
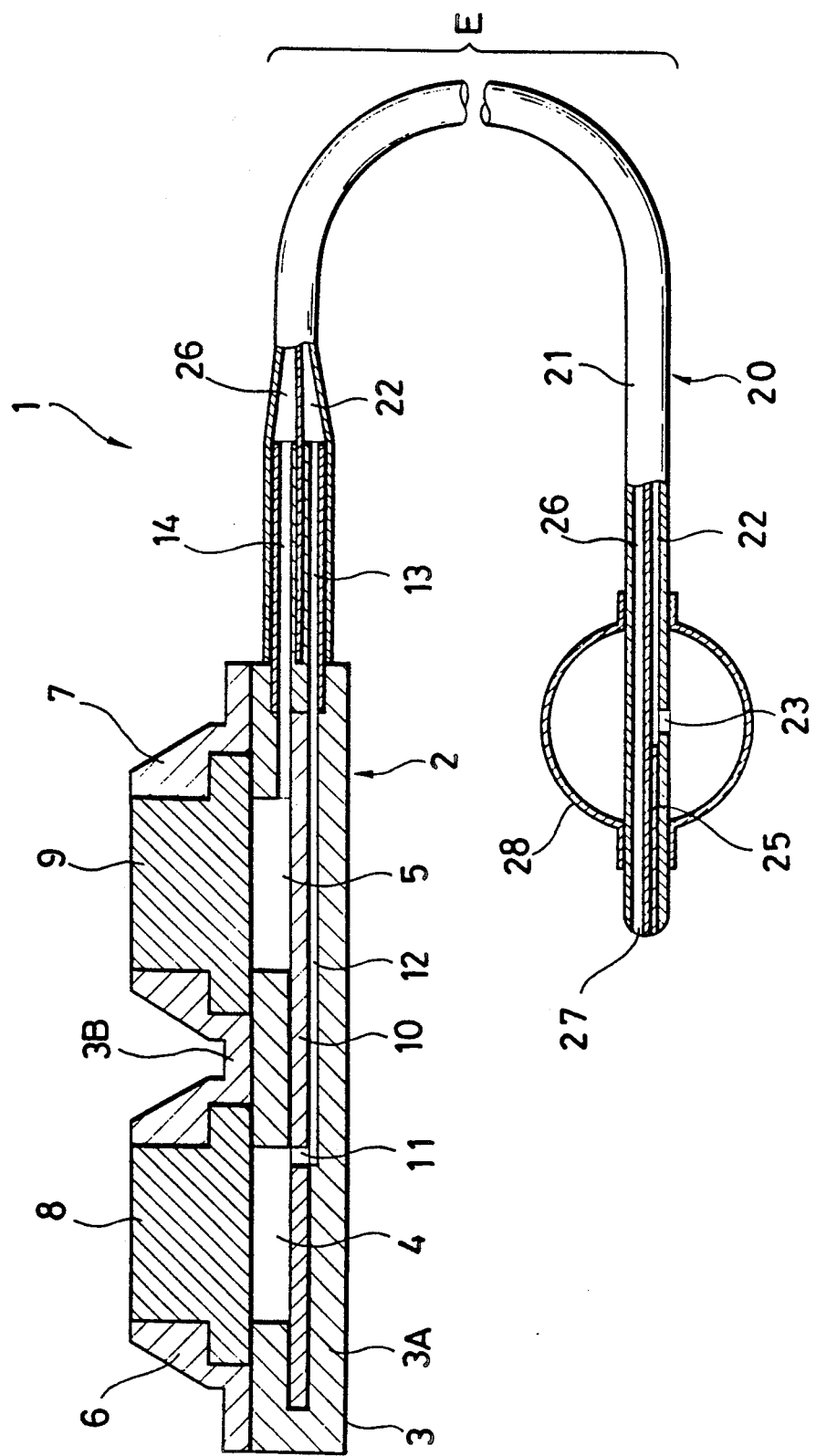
FIG. 2 is a cross section taken along lines II—II in FIG. 1.

FIG. 1 is a plan view of a hypodermically embedable catheter assembly according to the present invention, especially a hypodermically embedable catheter assembly having a balloon catheter, and FIG. 2 is an elevational cross-sectional view thereof.

As shown in the figures, the hypodermically embedable catheter assembly 1 includes a medicament infusion implement 2 and a balloon catheter 20 connected thereto. On use, the balloon catheter 20 is inserted into a blood vessel and indwelled therein while the medicament infusion implement 2 is embedded under the skin.

The medicament infusion implement 2 includes a housing 3 having a housing body 3A and a lid 3B, and the interior of the housing 3 is partitioned into first and second chambers 4 and 5. First and second inlet ports 6 and 7 are provided above the first and second chambers 4 and 5 in fluid communication therewith. The first and second inlet ports 6 and 7 allow for admission of different types of fluid, that is, a fluid for balloon expansion and a fluid medicament to be administered to the destined site as will be described later.

The first and second inlet ports 6 and 7 are preferably different in shape. More particularly, the first inlet port 6 along the edge has a rectangular configuration in plan view and the second inlet port 7 along the edge has a circular configuration in plan view as seen from FIG. 1.

The different configurations of the first and second inlet ports 6 and 7 make it possible to readily identify the first inlet port 6 (for balloon expansion) and the second inlet port 7 (for medicament infusion) by palpating them through the overlying skin when the medicament infusion implement 2 is recessed under the skin. A similar effect is achievable with other identifying means as by varying the height or dimensions of the first and second inlet ports 6 and 7.

Resilient members 8 and 9 are engaged in the first and second inlet ports 6 and 7, respectively. The resilient members 8 and 9 are of a material that can self close off after puncture, that is, can seal the puncture pore by itself to maintain gas tightness after a needle such as a puncture needle and venous needle has been inserted and withdrawn.

The material of which the resilient members 8 and 9 are formed include various rubbers such as silicone, isoprene and natural rubber, various resins such as polyurethane, polyamide elastomers, polybutadiene, and flexible vinyl chloride, and a mixture of two or more of them. Among others, silicone is preferred which is inert to the living body and experiences rather minimal changes in physical properties.

A plate-like needle stop 10 is disposed at the bottom of the housing 3 and opposed to the resilient members 8 and 9 for preventing the puncture needle punctured through the resilient member 8 or 9 from extending through the bottom of the housing 3.

The needle stop 10 may be formed of a rigid material, for example, metals such as stainless steel, titanium alloy, and brass, rigid resins such as polycarbonate, acryl, polypropylene and polyacetal, and ceramics of various compositions.

Instead of separately providing the needle stop 10, at least the portion of the housing bottom which is opposed to the resilient members 8 and 9 may be formed of a rigid material as mentioned above with similar results.

The housing 3 on one side is provided with first and second outlet ports 13 and 14 in fluid communication with the first and second chambers 4 and 5, respectively.

A passage 12 is defined between the needle stop 10 and the housing bottom, which has one end in fluid communication with the first chamber 4 through an aperture 11 in the needle stop 10 and another end in fluid communication with the first outlet port 13.

The first and second outlet ports 13 and 14 are of a configuration suitable for connection to first and second lumens 22 and 26 of the balloon catheter 20 to be described later, and in the illustrated embodiment, they are tubular members inserted a substantial distance into the respective lumens.

The first and second outlet ports 13 and 14 may be formed of a stiff material, for example, metals such as stainless steel, titanium alloy, brass, and chromium plated iron, and rigid resins such as polycarbonate, polypropylene, acryl, and polyacetal. The reason is that the outlet ports 13 and 14 should prevent a tube body 21 of the balloon catheter 20 connected thereto from being folded or turned, that is, provide such a degree of stiffness to ensure a flowpath against the resiliency of the balloon catheter 20. Therefore, the outlet ports 13 and 14 play the role of a buffer between the rigid housing 3 and the flexible tube body 21.

Further, the outlet ports 13 and 14 each may be furrowed on the outer surface to prevent easy withdrawal of the balloon catheter.

As shown in FIG. 1, the medicament infusion implement 2 at its four corners is provided with apertures 15 as retainer means for securing the implement to hypodermic tissues in the recess where the implement is embedded. The medicament infusion implement 2 is held in place by engaging a thread to each aperture 15 and tying it to a hypodermic tissue such as muscle.

The retainer means for securing the medicament infusion implement to hypodermic tissues in the recess where the implement is embedded is not limited to the above-mentioned one, but any other retainer means may be used, for example, forceps or clips capable of clamping hypodermic tissues.

The medicament infusion implement 2 may be fabricated by the following method, for example.

The housing body 3A is formed together with the outlet ports 13 and 14 and needle stop 10 by insert injection molding. The lid 3B with the first and second inlet ports 6 and 7 having the resilient members 8 and 9 engaged therein is then joined to the housing body 3A by bonding or fusion welding. For the bonding or fusion welding between the housing body 3A and the lid 3B, ultrasonic fusion welding is preferred for ease of operation although other means such as solvent bonding, adhesive bonding and thermowelding may also be employed.

The materials of which the housing body 3A and lid 3B are formed may be any desired materials as long as they are inert to the living body, and preferably selected from resins such as polypropylene, high density polyethylene, and polycarbonate and ceramics such as alumina and apatite. The materials of which the housing body 3A and lid 3B are formed may be the same or different.

As shown in FIGS. 1 and 2, the balloon catheter 20 has the tube body 21 having near its distal end (at the right in FIG. 1) a balloon 28 disposed around the outer peripheral wall of the tube body.

The balloon 28 is expandable (inflatable) and contractable since it is formed of a rubbery material such as silicone rubber and latex rubber or flexible vinyl chloride, polybutadiene, EVA (ethylene-vinyl acetate) or the like.

The tube body 21 is formed of a flexible material, for example, silicone rubber, vinyl chloride, polyurethane, polyethylene, polypropylene, nylon, and EVA.

It will be understood that the tube body 21 and the balloon 28 are preferably formed of a silicone rubber having good biological compatibility since they are inserted and left in the blood vessel. It is preferred that the tube body 21 and the balloon 28 are formed of the above-mentioned materials and treated to be antithrombotic since they are indwelled for a prolonged period.

The tube body 21 has first and second lumens 22 and 26 formed therein for the following purposes and functions.

The first lumen 22 communicates with the balloon 28 for expansion and contraction thereof. The outer periphery of the tube body 21 inside the balloon 28 is formed with a hole 23 in communication with the first lumen 22 while the first lumen 22 on a distal side with respect to the hole 23 is filled with a sealant 25 such as silicone rubber, polyurethane, and flexible vinyl chloride. It is to be noted that the sealant 25 may contain a radiopaque metal salt such as barium sulfate and bismuth oxide. Then the balloon 28 is expanded by admitting a fluid for balloon expansion into the first lumen 22 from the proximal end such that the fluid enters the balloon 28 through the first lumen 22 and hole 23 whereas the balloon 28 is contracted by removing the fluid.

The fluid for balloon expansion may include gases such as air, $CO_2$ gas, and $O_2$ gas and liquids such as physiological saline and radiographic contrast medium.

The second lumen 26 is open at the distal end of the tube body 21 for allowing a fluid to be injected into the body cavity or to be sucked in from the body cavity through the opening 27. More particularly, the lumen 26 is used for administering a fluid medicament to the destined site in the blood vessel where the balloon catheter 20 is inserted and indwelled.

Figure 3:
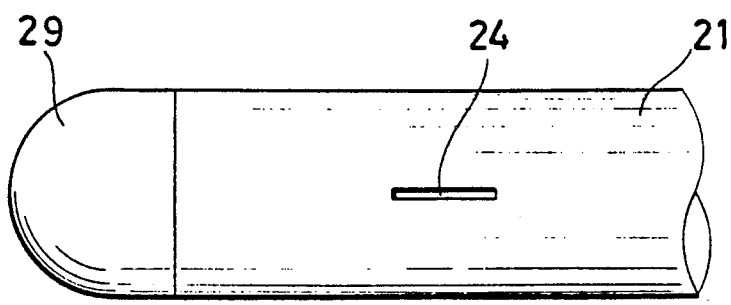
FIGS. 3 and 4 are plan and axial cross-sectional views showing the arrangement of the distal end of the balloon catheter according to the invention, respectively.
Figure 4:
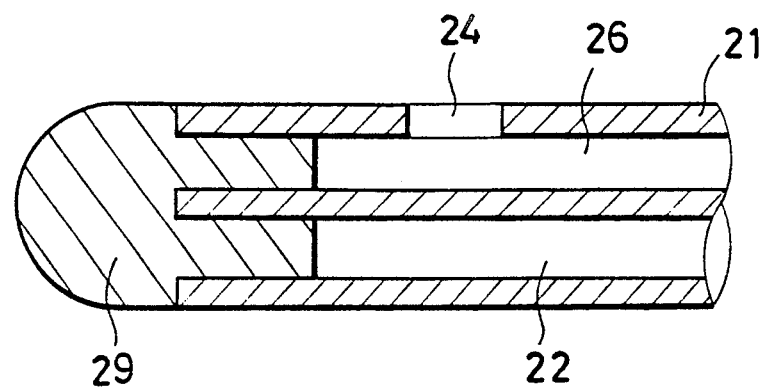

There is the risk that when no fluid medicament is administered, blood would enter the second lumen 26 through the opening 27 to form a thrombus, clogging the second lumen 26. A desirable countermeasure to this is to form a slit 24 in communication with the second lumen 26 instead of the opening 27 in the outer peripheral wall of the tube body 21 as shown in FIGS. 3 and 4 such that the medicament may be injected through the slit 24. The narrow slit does not allow blood to enter the second lumen 26, preventing thrombotic clogging of the second lumen 26.

In this embodiment, a plug 29 is engaged with the distal end of the tube body 21 for closing the first and second lumens 22 and 26.

The slit 24 is dimensioned such as to fully prevent entry of blood, but not to disturb injection of the fluid medicament, for example, to a slit width of 0 (sealed state) to about 0.01 mm and a slit length of about 1 to about 10 mm.

Two or more slits 24 may be formed in the tube body 21.

The slit 24 is usually disposed at a distal side end with respect to the balloon 28, but may be disposed at a proximal end with respect to the balloon 28 depending on the location where the balloon catheter 20 is to be indwelled. The terminology "distal" and "proximal" ends are conventionally used herein. The "proximal" end of the catheter is that end where it is connected to the medicament infusion implement, and the distal end of the catheter is that end where a balloon is attached thereto. The terms are used in this paragraph in a relative sense, as should be readily apparent.

The balloon 28 is usually disposed on a proximal end with respect to the opening 27 or slit 24 in the tube body 21. The balloon 28 is adapted to make close contact with the wall of the blood vessel when expanded, and plays not only the role of securing the balloon catheter 20 relative to the vessel, but also the role of shutting off the blood flow to prevent dilution with blood of the medicament which is injected through the opening 27 or slit 24 ahead of the balloon 28 (on the tube distal end).

The balloon 28 is preferably adapted to radially expand from the center of the tube body 21 when expanded.

The balloon 28 may have a circular, ellipsoidal or similar transverse cross section, but preferably a shape approximate to the transverse cross section of the blood vessel where it is to be inserted and indwelled because of enhanced tight contact with the vessel, that is, blood flow blockage.

It is possible to longitudinally arrange a plurality of such balloons along the tube body 21.

The balloon 28 should be attached to the tube body 21 in a gas or liquid tight manner. The attachment method may be any desired method capable of maintaining gas or liquid tightness of the balloon, including adhesive bonding of another member (such as an annular or tubular rubber member), tying with thread, and integral or two-color molding together with the tube.

The balloon catheter 20 of the above-mentioned construction is connected to the medicament infusion implement 2 such that at the proximal end, the first and second lumens 22 and 26 are in fluid communication with the first and second outlet ports 13 and 14, respectively.

When it is desired to hold the balloon catheter 20 in place for indwelling in the body, the balloon catheter 20 is preferably provided at an appropriate location on the proximal side with retainer means for securing the catheter to hypodermic tissues such as muscles.

One preferred example of the retainer means is the retainer ring disclosed in Japanese Patent Application Kokai No. 281965/1987 by the applicant.

Figure 5:
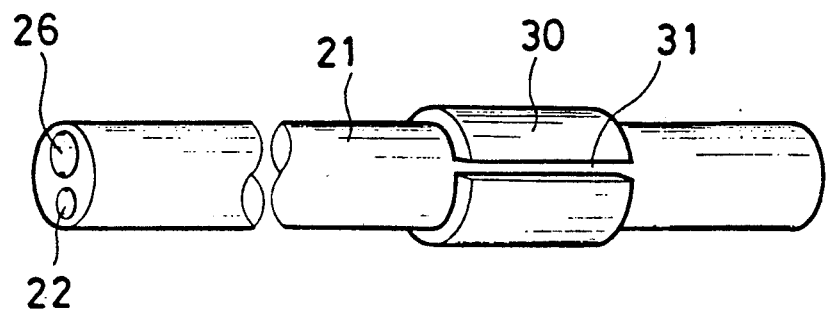
FIG. 5 is a perspective view showing the arrangement of a retainer ring mounted on the balloon catheter according to the present invention.

The retainer ring 30 is illustrated in FIG. 5 as a ring-like member having a slit 31 mounted on the outer periphery of the tube body 21.

The retainer ring 30 may preferably be mounted on the tube body 21 at any position within the region E shown in FIG. 2, more preferably at plural positions so as to prevent withdrawal of the catheter from the blood vessel because when the balloon catheter 20 is inserted and indwelled in the blood vessel, motion of the body can provide relative movement of the catheter and the body tissues causing the catheter to be withdrawn from the vessel. The retainer ring 30 is not limited to the illustrated configuration, and a ring having furrows on the outer periphery or the like may be employed.

Since the hypodermically embedable catheter assembly 1 is used by leaving it in the body, there is an increased need for carrying out medicament administration while identifying the location of the balloon catheter 20 under fluoroscopic observation. It is thus preferred to impart radiopaqueness to the balloon catheter 20. More particularly, it is preferred that the material of the tube body 21 and/or the balloon 28 contains a radiographic contrast agent. Examples of the radiographic contrast agent include metal salts such as barium sulfate and bismuth oxide.

Next, the operation of the hypodermically embedable catheter assembly 1 of the invention for embolic chemotherapy will be described.

The distal end of the balloon catheter 20 is inserted from the abdomen to the destined site in the arteria nutricia of the cancer carrying organ and indwelled thereat while the medicament infusion implement 2 is recessed beneath the abdomen skin where the balloon catheter is introduced. If necessary, the tube body 21 is secured to tissues like muscles by means of the retainer ring 30 on the tube body 21, and the medicament infusion implement 2 is secured to hypodermic tissues like muscles by means of apertures 15 at the four corners. The hypodermically embedable catheter assembly 1 is indwelled in this way without leaving any portion exposed outside the body surface.

If the first and second outlet ports 13 and 14 are formed of stiff material such as stainless steel, then clogging of the lumens 22 and 26 by folding of the tube body 21 is prevented.

The fluid medicament is administered to the destined site by the following procedure.

First the first inlet port 6 of the medicament infusion implement 2 is identified by palpating the ports through the overlying skin. A puncture needle of a syringe filled with a balloon expanding fluid is inserted through the resilient member 8 associated with the first inlet port 6 to admit the balloon expanding fluid into the first chamber 4. The inlet port can be selected without an error because the first and second inlet ports 6 and 7 have different shapes.

The balloon expanding fluid admitted into the first chamber 4 reaches the first outlet port 13 through the aperture 11 and the passage 12, passes through the first lumen 22, and then enters the balloon 28 through the hole 23, causing the balloon 28 to expand to the predetermined size. Expansion of the balloon 28 shuts off further blood flow through the vessel.

After the balloon 28 has been expanded, the puncture needle is withdrawn from the resilient member 8.

The resilient member 8 self closes off after withdrawal of the puncture needle, maintaining the balloon 28 expanded.

Then the second inlet port 7 of the medicament infusion implement 2 is identified by palpating the ports through the overlying skin. A puncture needle of a syringe filled with a fluid medicament to be administered (for example, carcinostatic agent) or a venous needle connected to a fluid bottle through a tube is inserted through the resilient member 9 associated with the second inlet port 7 to admit the fluid medicament into the second chamber 5. The medicament thus admitted is conducted through the second outlet port 14 and second lumen 26 and injected to the destined site through the opening 27 at the distal end.

When the slit 24 shown in FIGS. 3 and 4 is provided instead of the opening 27, the pressure of the medicament admitted causes the slit 24 to open, allowing the medicament reject therethrough. Since the slit 24 is closed in the absence of a medicament to be admitted, no blood will enter the second lumen 26 through the slit 24, preventing clogging of the second lumen 26 by thrombus formation.

Since the blood flow in the vessel is shut off by the expanded balloon 28, the medicament introduced to the destined site is taken in by cancer cells without dilution with blood.

At the end of medicament administration, the puncture needle is withdrawn from the resilient member 9. No leakage of the fluid medicament occurs because the resilient member 9 closes off by itself after withdrawal of the puncture needle.

In inserting the syringe puncture needle or venous needle throughout the resilient member 8 or 9, the needle stop 10 disposed at the housing bottom at positions opposed to the resilient members 8 and 9 prevents the needle from extending throughout the housing.

After a predetermined time (usually approximately 30 minutes) has passed since administration of the medicament, a puncture needle of a syringe is inserted through the resilient member 8 associated with the first inlet port 6 to suck up the balloon expanding fluid from the first chamber 4, causing the balloon 28 to contract and allowing the blood to flow again.

Before or after this step, a radiopaque agent may be admitted into the vessel through the second inlet port 7 by the same procedure as the medicament admission in order to examine the therapeutic effect. Advantageously a clear radiographic image is obtained at this point because the blood flow is shut off and the radiopaque agent is not diluted with blood.

If the balloon catheter 20 is radiopaque, the fluid medicament can be administered while the location of the balloon catheter 20 is identified under fluoroscopic observation.

The treatment is repetitively carried out in this way every several days or several weeks.

In the prior art practice, the balloon catheter is inserted and withdrawn every time when treatment is to be carried out, imposing a substantial burden to the patient. Percutaneous insertion of the balloon catheter leaves the risk of infection. On the contrary, the present invention allows the treatment to be repetitively carried out any desire times while the catheter assembly of the hypodermic embedment type is kept indwelled in the body, minimizing the burden to the patient. The catheter assembly of the hypodermic embedment type leaves no risk of infection throughout the therapeutic period because it is no longer exposed outside the skin surface. This allows the patient to act freely and even take a bath.

Figure 6:
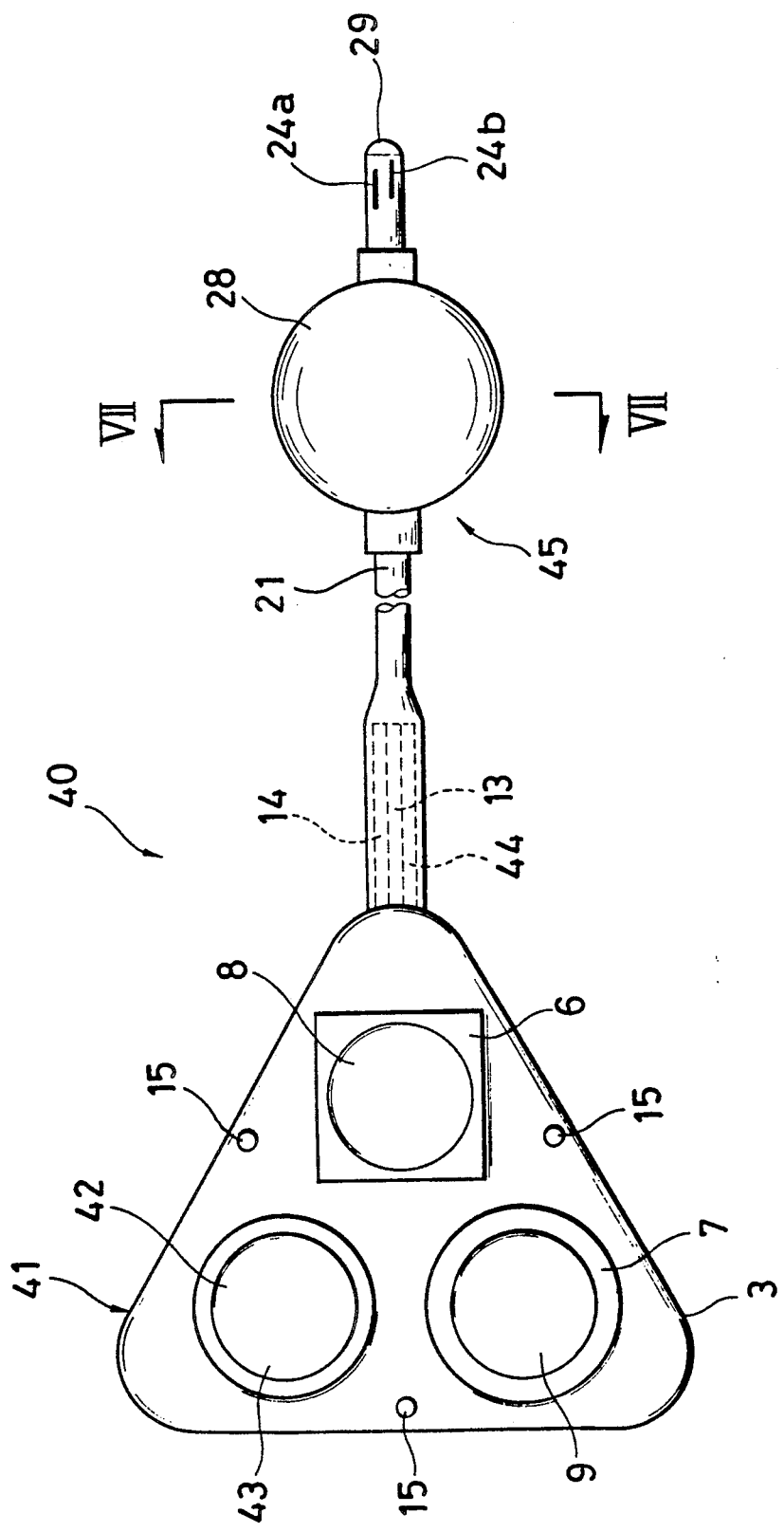
FIG. 6 is a plan view of a catheter assembly of the hypodermic embedment type according to another embodiment of the present invention.
Figure 7:
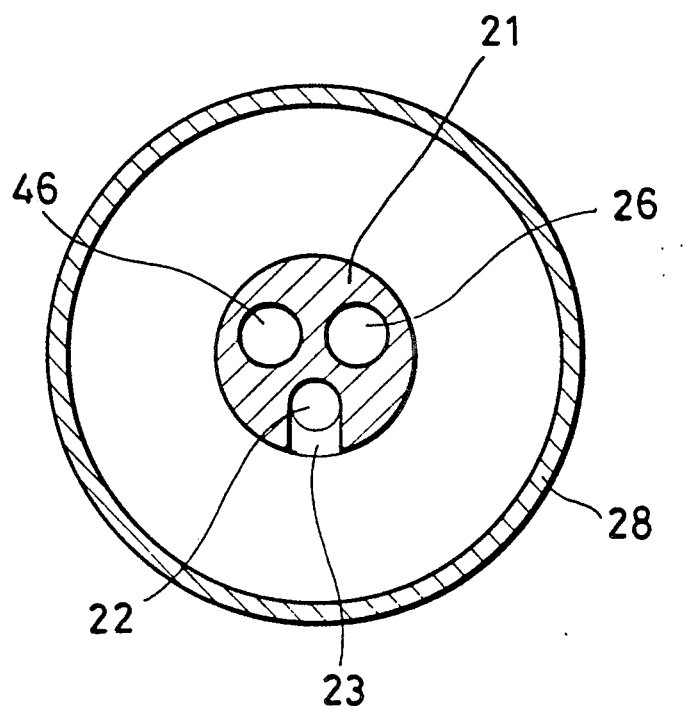
FIG. 7 is a cross section taken along lines VII—VII in FIG. 6.

FIG. 6 is a plan view of a hypodermically embedable catheter assembly according to another embodiment of the present invention, and FIG. 7 is a cross sectional view taken along lines VII—VII in FIG. 6. The construction and operation of the hypodermically embedable catheter assembly shown in these figures are now described by only referring to the differences from the previous embodiment with the remaining similar descriptions omitted.

In these figures, those parts having the same function as in the previous embodiment are designated by the same reference numerals.

The hypodermically embedable catheter assembly 40 shown in FIG. 6 includes a medicament infusion implement 41 having a triangular housing 3 of such a material as described in the previous embodiment, which housing is divided into three chambers, first, second, and third chambers.

First, second and third inlet ports 6, 7 and 42 are provided in an upper portion of the housing 3 in fluid communication with the first, second and third chambers.

The first port 6 is for balloon expansion. The second and third inlet ports 7 and 42 are for admission of fluid medicaments. Preferably different medicaments are administered through these inlet ports.

The first, second and third inlet ports 6, 7 and 42 are preferably different in shape or height so that they can be identified from each other by palpation when the medicament infusion implement 41 is hypodermically recessed. In the illustrated embodiment, the first inlet port 6 has a rectangular configuration, and the second and third inlet ports 7 and 42 have a circular configuration, but are different in height.

Resilient members 8, 9 and 43 are engaged in the first, second and third inlet ports 6, 7 and 42, respectively, as in the previous embodiment.

The housing 3 at one side has first, second and third outlet ports 13, 14 and 44 in fluid communication with the first, second, and third chambers, respectively.

In turn, the balloon catheter 45 has a balloon 28 as in the previous embodiment and includes a tube body 21 having first, second and third lumens 22, 26 and 46 formed therein (see FIG. 7).

The first lumen 22 provides a flowpath for an expanding fluid for the balloon 28 whereas the second and third lumens 26 and 46 are for introducing fluid medicaments into the body cavity.

Thus the first lumen 22 at a proximal end is connected to the first outlet port 13, the second lumen 26 at a proximal end is connected to the second outlet port 14, and the third lumen 46 at a proximal end is connected to the third outlet port 44.

Further, the outer periphery of the tube body 21 on a distal side with respect to the balloon 28 is formed with slits 24a and 24b in fluid communication with the second and third lumens 26 and 46, respectively. These slits 24a and 24b are the same as the slit 24 previously described.

Then a fluid medicament can be introduced from the second inlet port 7, passed through the second chamber of the housing 3, the second outlet port 14 and the second lumen 26 and injected through the slit 24a, and another fluid medicament can be introduced from the third inlet port 42, passed through the third chamber of the housing 3, the third outlet port 44 and the third lumen 46 and injected through the slit 24b.

The hypodermically embedable catheter assembly 40 of the above illustrated construction allows different types of medicament to be admitted into the body through discrete passages.

A first advantage is that where fluids A and B are incompatible, that is, property change, deterioration, or precipitation occurs in a mixture of fluids A and B which are kept mixed in ambient air, it is possible to introduce fluids A and B into the body cavity without property change, deterioration, or precipitation by separately admitting fluid A through the second inlet port 7 and fluid B through the third inlet port 42 and causing fluids A and B to be injected through the slits 24a and 24b whereby fluids A and B are mixed in the body cavity.

Examples of such medicaments are combinations of antibiotics (synthetic penicillin, glypenin, etc.) and amino acid preparations, etc.

A second advantage is that the assembly can accommodate a situation where it is desired to infuse different types of medicament at different flow rates.

In one example, fluid A is admitted at 1000 ml/min. and fluid B is admitted at 0.05 ml/min. It is possible to independently control the rates of medicament fluids admitted as by reducing or stopping admission of fluid B while continuing admission of fluid A upon occurrence of an abnormal situation, for example, a blood pressure rise.

The present invention is not limited to the above-illustrated embodiments. For example, the number of inlet and outlet ports in the medicament infusion implement and the number of chambers in the housing are not limited to the illustrated embodiments. As to the balloon catheter, any desired construction commonly used in the art is applicable.

The construction of the hypodermically embedable catheter assembly having the balloon catheter has been described although the invention is, of course, applicable to an assembly having a catheter without a balloon.

INDUSTRIAL APPLICABILITY

While maintaining an advantage associated with embolic chemotherapy that a medicament fluid in a high concentration can be directly infused to the destined site, the hypodermically embedable catheter assembly of the present invention allows therapeutic treatment to be repeatedly carried out any desired times in a simple manner with the hypodermically embedable catheter assembly kept indwelled in the body, significantly reducing the burden to the patient as compared with the prior art technique where the catheter must be inserted and withdrawn every time when treatment is to be carried out.

In addition, as opposed to the prior art technique wherein the catheter is percutaneously introduced, the hypodermically embedable catheter assembly of the present invention eliminates the risk of infection during the therapeutic period because the assembly is used in a state that its entirety is indwelled in the body without being exposed outside the body surface.

I claim:

1. A catheter assembly of the hypodermic embedment type, which is used by being embedded in its entirety under the skin, the assembly comprising:

a hypodermically embedable medicament infusion implement including a housing and at least one inlet port and at least one outlet port, said at least one inlet port and at least one outlet port being in communication with said housing; and a balloon catheter having distal and proximal ends, and having a balloon at said distal end thereof;

said at least one outlet port of said medicament infusion implement connected to said proximal end of said catheter;

said at least one inlet port has mounted therein a resilient member which allows insertion of a needle and which self closes off after withdrawal of the needle;

said medicament infusion implement further including a first chamber for balloon inflation and a second chamber for medicament infusion defined in said housing, a first inlet port and a first outlet port in communication with said first chamber, and a second inlet port and a second outlet port in communication with said second chamber;

said first and second inlet ports having at least one dimension which is different from each other;

said balloon catheter including a tube body having a distal end, at least one expandable and contractible balloon disposed around the periphery of said tube body near said distal end of said tube body, a first lumen formed in said tube body in communication with said balloon, and a second lumen formed in said tube body and opening at a further distal end portion of said tube body beyond said balloon; and said first lumen having a proximal end connected to said first outlet port and said second lumen having a proximal end connected to said second outlet port.

2. The catheter assembly of claim 1, wherein said first and second inlet ports having a different shape.

3. The catheter assembly of claim 1, wherein said first and second inlet ports have a different height.

4. The catheter assembly of claim 1, wherein said first inlet port is generally rectangular in plan view and said second inlet port is generally circular in plan view.

5. The catheter assembly of claim 1, wherein said medicament infusion implement includes at least two inlet ports and at least two outlet ports for fluid medicament infusion.

6. The catheter assembly of claim 1, wherein said second lumen has an open end, said open end of said second lumen including a slit-like opening in an outer wall portion of said tube body.

7. The catheter assembly of claim 1, wherein:

said medicament infusion implement further includes a third chamber for medicament infusion defined in said housing; and a third inlet prot and a third outlet port in communication with said third chamber;

said balloon catheter further includes a third lumen formed in said tube body and opening at said further distal end portion of said tube body beyond said balloon; and said third lumen having a proximal end connected to said third outlet port.

8. The catheter assembly of claim 7, wherein said first, second, and third inlet ports all have at least one dimension which is different from each other.

9. The catheter assembly of claim 8, wherein said first, second, and third inlet ports have respective different shapes.

10. The catheter assembly of claim 8, wherein said first, second, and third inlet ports have respective different heights.

11. The catheter assembly of claim 8, wherein said second and third lumens each having respective open ends, said open ends of said second and third lumens including a slit-like opening in and outer wall portion of said tube body.

12. The catheter assembly of claim 7, wherein said second and third lumens each have respective open ends, said open ends of said second and third lumens including a slit-like opening in an outer wall portion of said tube body.

13. The catheter assembly of claim 1, wherein a portion of said housing opposed to said resilient member is provided with a needle stop which prevents insertion of a needle therethrough.

14. The catheter assembly of claim 13, wherein said needle step comprises a hard material for preventing insertion of a needle therethrough.

15. The catheter assembly of claim 7, wherein a portion of said housing opposed to said resilient member is provided with a needle stop which prevents insertion of a needle therethrough.

16. The catheter assembly of claim 13, wherein said medicament infusion implement includes securing means for retaining the implement to hypodermic tissues in a recess of a body where the implement is to be embedded.

17. The catheter assembly of claim 7, wherein said medicament infusion implement includes securing means for retaining the implement to hypodermic tissues in a recess of a body where the implement is to be embedded.

18. The catheter assembly of claim 1, wherein said medicament infusion implement includes securing means for retaining the implement to hypodermic tissues in a recess of a body where the implement is to be embedded.

* * * * *